US012578322B2

(12) United States Patent
Doney et al.

(10) Patent No.: US 12,578,322 B2
(45) Date of Patent: Mar. 17, 2026

(54) METHODS AND CONSUMER PRODUCTS FOR DETECTING A METABOLITE

(71) Applicant: Kimberly-Clark Worldwide, Inc., Neenah, WI (US)

(72) Inventors: Elizabeth M. Doney, Appleton, WI (US); Kathleen C. Engelbrecht, Kaukauna, WI (US); David W. Koenig, Menasha, WI (US); Stephen Quirk, Alpharetta, GA (US); Kassi Kosnicki, La Mesa, CA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 345 days.

(21) Appl. No.: 18/034,779

(22) PCT Filed: Dec. 7, 2020

(86) PCT No.: PCT/US2020/063592
§ 371 (c)(1),
(2) Date: May 1, 2023

(87) PCT Pub. No.: WO2022/125057
PCT Pub. Date: Jun. 16, 2022

(65) Prior Publication Data
US 2023/0417734 A1 Dec. 28, 2023

(51) Int. Cl.
*G01N 33/493* (2006.01)
*G01N 30/88* (2006.01)
*G01N 30/72* (2006.01)

(52) U.S. Cl.
CPC ........... *G01N 33/493* (2013.01); *G01N 30/88* (2013.01); *G01N 30/72* (2013.01); *G01N 2030/8813* (2013.01); *G01N 2030/8831* (2013.01)

(58) Field of Classification Search
CPC ...... G01N 33/493; G01N 30/88; G01N 30/72; G01N 2030/8813; G01N 2030/8831
See application file for complete search history.

(56) References Cited

U.S. PATENT DOCUMENTS

| | | | |
|---|---|---|---|
| 5,789,442 | A | 8/1998 | Garfield et al. |
| 6,469,016 | B1 | 10/2002 | Place et al. |

(Continued)

FOREIGN PATENT DOCUMENTS

| | | |
|---|---|---|
| EP | 1199069 B1 | 5/2002 |
| KR | 20190045841 A | 5/2019 |

(Continued)

OTHER PUBLICATIONS

Dokumacioglu, Eda et al., "Measuring urinary 8-hydroxy-2'-deoxyguanosine and malondialdehyde levels in women with over-active bladder," Investigative and Clinical Urology, vol. 59, 2018; https://doi.org/10.4111/icu.2018.59.4.252; pp. 252-256.

(Continued)

*Primary Examiner* — Benjamin R Schmitt
(74) *Attorney, Agent, or Firm* — Armstrong Teasdale LLP

(57) ABSTRACT

Methods and consumer products for detecting a metabolite, the method comprising: testing a urine sample from a subject for a metabolite selected from the group consisting of androstenediol, oxtenedioate, digydrouracil, heptanoyl-glutamine, pregnenetriol, sulfate, heptenoylglutamine, hexanoylglutamine, guanine, methylhexanoylglutamine, hexanoylglycine, hexenoylglycine, spermidine, diacetyl-spermine, acisoga and combinations thereof; and producing a metabolic profile for the metabolite.

10 Claims, 1 Drawing Sheet

(56) References Cited

U.S. PATENT DOCUMENTS

| | | | |
|---|---|---|---|
| 6,689,809 | B2 | 2/2004 | Ahotupa et al. |
| 6,995,150 | B2 | 2/2006 | Labrie |
| 7,763,284 | B2 | 7/2010 | Kim et al. |
| 8,962,693 | B2 | 2/2015 | Santti et al. |
| 9,433,595 | B2 | 9/2016 | Kim et al. |
| 9,673,030 | B2 | 6/2017 | Jones et al. |
| 10,539,575 | B2 | 1/2020 | Perichon et al. |
| 2002/0128276 | A1 | 9/2002 | Day et al. |
| 2004/0146894 | A1 | 7/2004 | Warrington et al. |
| 2007/0128589 | A1 | 6/2007 | Sanders et al. |
| 2008/0032959 | A1 | 2/2008 | Alves et al. |
| 2012/0040383 | A1 | 2/2012 | Jia et al. |
| 2013/0065320 | A1 | 3/2013 | Fedorak et al. |
| 2016/0106702 | A1 | 4/2016 | Narayanan et al. |
| 2019/0094205 | A1 | 3/2019 | Sakairi |
| 2019/0310269 | A1 | 10/2019 | Cirulli et al. |
| 2019/0391092 | A1 | 12/2019 | Robinson et al. |

FOREIGN PATENT DOCUMENTS

| | | |
|---|---|---|
| WO | 2018184112 A1 | 10/2018 |
| WO | 2019074757 A1 | 4/2019 |

OTHER PUBLICATIONS

Wein, Alan J., et al., "Overactive Bladder: A Better Understanding of Pathophysiology, Diagnosis and Management," The Journal of Urology, vol. 175, Mar. 2006; doi:10.1016/S0022-5347(05)00313-7; pp. S5-S10.

Traish, Abdulmaged, M., PhD et al., "Role of Androgens in Female Genitourinary Tissue Structure and Function: Implications in the Genitourinary Syndrome of Menopause," Sexual Medicine Reviews, 2018; pp. 558-571.

Bray, Rhiannon et al., "Urinary metabolic phenotyping of women with lower urinary tract symptoms," Journal of Proteome Research, vol. 16, No. 11, 2017; https://doi.org/10.1021/acs.jproteome.7b00568; pp. 4208-4216.

Hao, Ling et al., "In-Depth Characterization and Validation of Human Urine Metabolomes Reveal Novel Metabolic Signatures of Lower Urinary Tract Symptoms," Scientific Reports, vol. 6, No. 1, 2016; https://doi.org/10.1038/srep30869; pp. 1-11.

Karstens, Lisa et al., "Does the Urinary Microbiome Play a Role in Urgency Urinary Incontinence and its Severity?," Frontiers in Cellular and Infection Microbiology, vol. 6, Article 78, Jul. 2016; https://doi.org/10.3389/fcimb.2016.00078; 13 pp.

Segata, Nicola et al., Metagenomic biomarker discovery and explanation, Genome Biology, vol. 12, 2011; http://genomebiolog.com/2011/11/6/R60; 18 pp.

Wu, Peng et al., "Urinary Microbiome and Psychological Factors in Women with Overactive Bladder," Frontiers in Cellular and Infection Microbiology, vol. 7, Article 488, Nov. 2017; https://doi.org/10.3389/fcimb.2017.00488; 11 pp.

Thomas-White, Krystal et al., " Bladder and Vaginal Microbiomes Have a Corresponding Shift Following Estrogem Treatment in Post-Menopausal Women," The FASEB Journal, vol. 31, Issue S1, Oct. 2018; pp. 940.4 (graphic abstract only).

Shimura, Hiroshi et al., "Metabolomic Analysis of Overactive Bladder in Male Patients: Identification of Potential Metabolite Biomarkers," Urology 118, 2018; https://doi.org/10.1016/j.urology.2018.05.001; pp. 158-163.

Peng, Jun et al., Development of a Universal Metabolome-Standard Method for Long-Term LC-MS Metabolome Profiling and Its Application for Bladder Cancer Urine-Metabolite-Biomarker Discovery, Analytical Chemistry, vol. 86, 2014; dx.doi.org/10.1021/acs5011684; pp. 6540-6547.

Thomas-White, Krystal J et al., " Incontinence Medication Response Relates to the Female Urinary Microbiota," Int Jrogynecol J, vol. 27, No. 5, May 2016; doi:10.1007/s00192-015-2847-x; pp. 723-733.

Bai, Sang Wook et al., " Relationship between Urinary Endogenous Steroid Metabolites and Lower Urinary Tract Function in Post-menopausal Women," Yonsei Medical Journal, vol. 44, No. 2, 2003; pp. 279-287.

Bai, S.W et al., "Relationship between Urinary Profile of the Endogenous Steroids and post menopausal Women with Stress Urinary Incontinence," Neurology and Urodynamics vol. 22, 2003; pp. 198-205.

Teleman, Pia M., et al., The relation between urinary incontinence and steroid hormone levels in perimenopausal women. A report from the Women's Health in the Lund Area (WHILA) study; Acta Obstetricia et Gynecologica, vol. 88. 2009; pp. 927-932.

International Search Report and Written Opinion for Patent Application PCT/US2020/063592 mailed Aug. 31, 2021; 13 pp.

Shackleton, Cedric H.L. et al., "Androstanediol and 5-androstenediol profiling for detecting exogenously administered dihydrotestosterone, epitestosterone, and dehydroepiandrosterone: Potential use in gas chromatography isotope ratio mass spectrometry", Steroids, vol. 62, 1997, pp. 665-673.

Mazzarino, Monica et al., "Relevance of the selective oestrogen receptor modulators tamoxifen, toremifene and clomiphene in doping field: Endogenous steroids urinary profile after multiple oral doses", Steroids, vol. 76, 2011, pp. 1400-1406.

Parr, Maria K. et al., "Seized designer supplement named "1-Androsterone": Identification as 3b eta-hydroxy-5 alpha-androst-1-en-17-one and its urinary elimination", Steroids, vol. 76, 2011, pp. 540-547.

Saudan, Christophe et al., "Urinary marker of oral pregnenolone administration", Steroids, vol. 70, 2005, pp. 179-183.

Saudan, Christophe et al., "Longitudinal profiling of urinary steroids by gas chromatography/combustion/isotope ratio mass spectrometry: Diet change may result in carbon isotopic variations" Journal of Chromatography B, vol. 831, 2006, pp. 324-327.

Examination Report for GB Patent Application No. GB2309860.1 dated Sep. 20, 2024; 7 pp.

Notice of Preliminary Rejection for KR Patent Application No. 10-2023-7022006 dated Nov. 22, 2023; 5 pp.

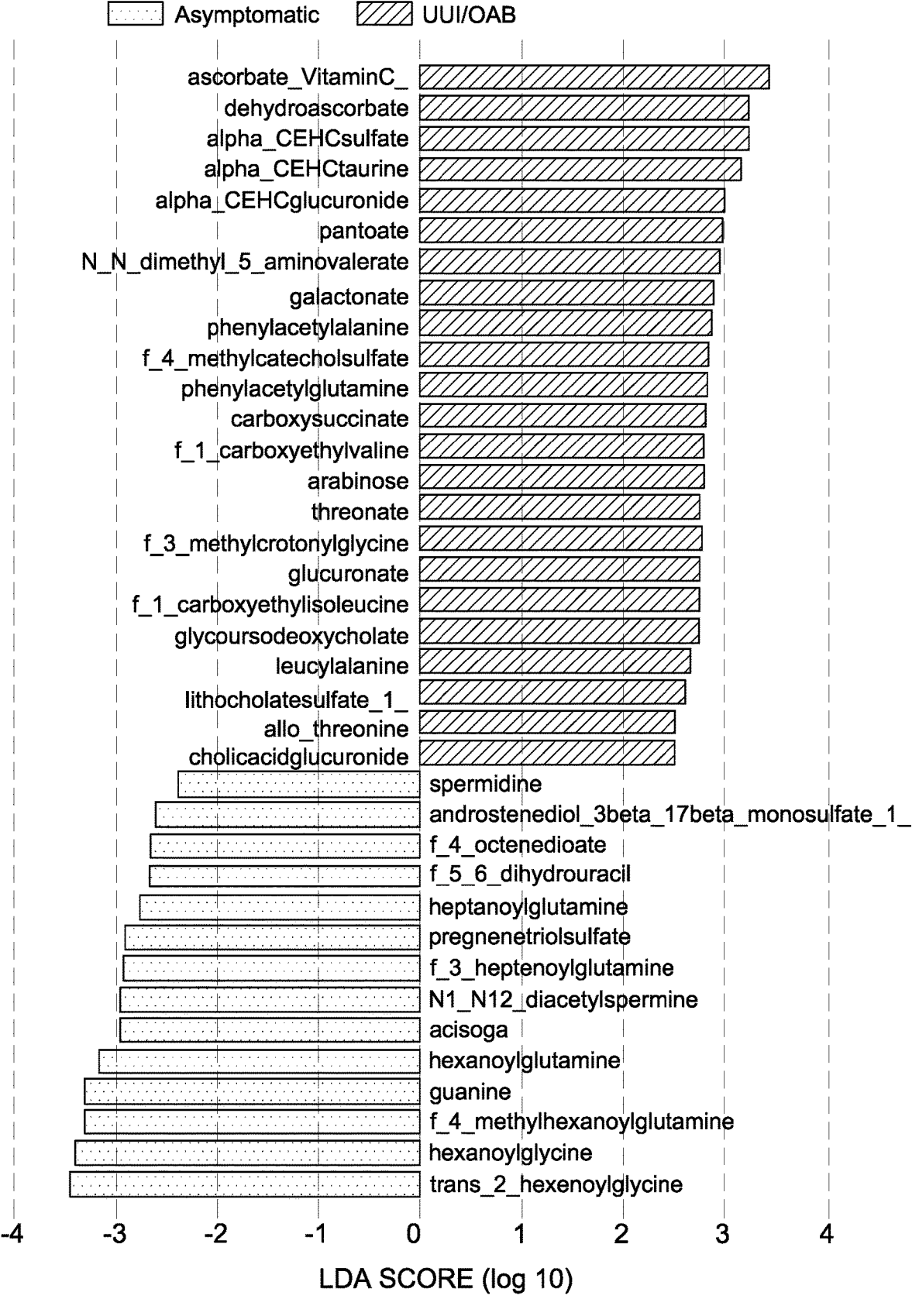

METHODS AND CONSUMER PRODUCTS FOR DETECTING A METABOLITE

CROSS-REFERENCE TO RELATED APPLICATION

This application is a U.S. National Phase Application of PCT/US2020/063592, filed Dec. 7, 2020, the content of which is hereby incorporated by reference in its entirety.

FIELD OF DISCLOSURE

This disclosure is directed to methods and consumer products for detecting a metabolite.

BACKGROUND

Lower-urinary tract symptoms (LUTS), such as overactive bladder (OAB) and urinary urge incontinence (UUI) affect half of women worldwide. These symptoms are often attributed to involuntary bladder muscle contractions caused by abnormal neuromuscular signaling; however, only half of all women with incontinence experience involuntary bladder muscle contractions, suggesting other underlying causes. When women seek treatment, a group of physical, chemical, and microscopic tests, known as a urinalysis, is performed on a patient's urine. Unfortunately, urinalysis alone does not differentiate between healthy and incontinent subjects or target the underlying causes of these diseases. Further, urinalysis fails to provide a prognosis that improves a patient's quality of life.

To improve the effectiveness of prognosis and prevent bladder leakage, it is important to understand physiological mechanisms occurring in the bladder and how these factors may influence LUTS. Metabolic analysis may be used to obtain metabolic profiles of urine and investigate the underlying mechanisms. However, typical clinical urinalysis does not provide adequate data to study these mechanisms.

In general, most of the research analyzing the urine metabolome has differentiated healthy subjects from subjects with other conditions, such as bladder cancer and diabetes. The little research that has analyzed the urine metabolome in relation to LUTS has been performed mainly in men with urine collected from mid-stream urine samples instead of urine collected directly from the bladder.

It was surprisingly found in the present disclosure that a metabolic profile including multiple novel metabolites could be used to characterize LUTs.

Described herein are methods and consumer products for detecting a metabolite. A metabolic profile n ay be produced and used for a variety of purposes.

Objective of the Disclosure

The aim of the present disclosure is to provide methods and consumer products for detecting a metabolite and producing metabolic profiles related to lower urinary tract symptoms.

BRIEF DESCRIPTION OF THE DISCLOSURE

In one aspect, provided herein is a method of detecting a metabolite, the method comprising (i) testing a urine sample from a subject for a metabolite selected from the group consisting of androstenediol, octenedioate, dihydrouracil, heptanoylglutamine, pregnenetriol sulfate, heptenoylglutamine, hexanoylglutamine, guanine, methylhexanoylglutamine, hexanoylglycine, hexenoylgycine spermidine, diacetylspermine, acisoga, and combinations thereof; and (ii) producing a metabolic profile for the metabolite.

In another aspect, provided herein is a consumer product for use in assessing bladder health of a subject, the consumer product comprising a sensor configured to test a urine sample from the subject for a metabolite selected from the group consisting of androstenediol, octenedioate, dihydrouracil, heptanoylglutamine, pregnenetriol sulfate, heptenoylglutamine, hexanoylglutamine, guanine, methylhexanoylglutamine, hexanoylglycine, hexenoylgycine, spermidine, diacetylspermine, acisoga, and combinations thereof.

BRIEF DESCRIPTION OF THE DRAWINGS

FIG. 1 is an exemplary embodiment in accordance with the present disclosure depicting the relative expression of 37 metabolites in subjects with UUI/OAB compared to healthy, asymptomatic subjects.

DETAILED DESCRIPTION OF THE DISCLOSURE

Generally, the methods of detecting a metabolite according to the present disclosure comprise analyzing urine. In many embodiments, the methods of detecting a metabolite according to the present disclosure comprise (i) testing a urine sample from a subject for a metabolite selected from the group consisting of androstenediol, octenedioate, dihydrouracil, heptanoylglutamine, pregnenetriol sulfate, heptenoylglutamine, hexanoylglutamine, guanine, methythexanoylglutamine, hexanoylglycine, hexenoylgycine, sperruidine, diacetylspermine, acisoga, and combinations thereof; and (ii) producing a metabolic profile for the metabolite.

The metabolite may indicate the presence of a lower urinary tract symptom. Such lower urinary track symptoms include overactive bladder and urinary urge incontinence.

The metabolite may indicate the presence of an underlying cause of a lower urinary tract symptom.

As shown in FIG. 1, the select metabolites according to the present disclosure are expressed less in subjects with UUI/OAB. Thus, the is may be used to different healthy, asymptomatic subjects and subjects with UUI/OAB. The metabolites may also be used to differentiate various presentations, states, and/or forms of UUI/OAB in subjects.

As used herein, a metabolic profile is an array of the expression of one or more metabolites. The expression can be as measured, relative to the expression of other metabolites, and/or relative to the expression of the same or different metabolites in a different individual.

In many embodiments, the metabolic profile of the subject may be compared to a metabolic profile of a different subject. The metabolic profile of the subject may be compared to a metabolic profile for a healthy subject or a subject with a disease through a method selected from statistical analysis, by taking a ratio of the metabolic profiles, and combinations thereof.

The metabolic profile may be used for a variety of purposes. The metabolic profile may be used to assess the health of the subject, monitor the health of the subject, predict risk for a disease, determine whether intervention is needed to prevent a disease, provide an early indication of risk for a disease, study a disease, study an underlying cause of a disease, diagnose a disease, or provide a prognosis for a disease. Metabolic profiles gathered over time may be used to monitor and/or study the health of the subject over time.

Testing can occur for any number of the select metabolites. Testing may include testing for at least two metabolites, at least three metabolites, at least four metabolites, at least five metabolites, at least six metabolites, at least seven metabolites, at least eight metabolites, at least nine metabolites, at least ten metabolites, at least eleven metabolites, at least twelve metabolites, at least thirteen metabolites, at least fourteen metabolites, at least fifteen metabolites, at least sixteen metabolites, at least seventeen metabolites, at least eighteen metabolites, at least nineteen metabolites, at least twenty metabolites, or at least twenty-one metabolites. In some preferred embodiments, testing includes testing for at least three metabolites.

A metabolic profile for at least three metabolites is advantageous compared to a metabolic profile for one or two metabolites because the additional metabolic information may provide more robust confirmation of a disease state and/or information regarding the underlying cause of a disease state. The additional metabolic information may also be used to differentiate different presentations and/or forms of a disease state.

Testing may include testing for a metabolite selected from the group consisting of androstenediol, octenedioate, dihydrouracil, heptanoylglutamine, pregnenetriol sulfate, heptenoylglutamine, hexanoylglutamine, guanine, methylhexanoylglutamine, hexanoylglycine, hexenoylgycine, spermidine, diacetylspermine, acisoga, and combinations thereof.

Testing may include testing for a metabolite selected from the group consisting of androstenediol, octenedioate, dihydrouracil, heptanoylglutamine, pregnenetriol sulfate, heptenoylglutamine, hexanoylglutamine, guanine, methylhexanoylglutamine, hexanoylglycine, hexenoylgycine, and combinations thereof.

Testing may include testing for androstenediol.

The metabolites may be present in a range of expression ratios relative to metabolites represented in symptomatic subjects. In some embodiments, each metabolite is present in an expression ratio of at least 1.0. In some embodiments, each metabolite is present in an expression ratio of art least 1.25. In some embodiments, each metabolite is present in an expression ratio of at least 2.5.

The metabolites may be presenting a range of concentrations. In some embodiments, each metabolite is present in an amount of at least 1 ng/L.

In many embodiments, the subject is an animal subject, a human subject, or a non-human animal subject. The subject may be any age or gender. Non-limiting examples include male children, female children, male adults, female adults, elderly males, and elderly females. In some embodiments, the subject is a human subject. In some preferred embodiments, the subject is a human female subject. In some preferred embodiments, the subject is a postpartum or premenopausal human female subject. Metabolic signatures may differ based on age and/or gender.

In many embodiments, the methods according to the present disclosure further comprise communicating the metabolic profile. The metabolic profile may be communicated to an individual using a consumer product configured for testing urine. The metabolic profile may be communicated to an individual testing their own urine or testing the urine of another individual. The metabolic profile may be communicated generally to the environment of testing. The metabolic profile may be communicated to an electronic device through a wired, wireless, and/or Internet connection.

Communication may include sensory means of communication, including visual and/or audio signals. For example, visible signals may include a color change, a shape change, a readout, a written message, an electronic display, a printed display, and combinations thereof. Audio signals may include sounds and spoken words.

In many embodiments, the methods according to the present disclosure comprise obtaining a urine sample from a subject. A urine sample may be obtained from a subject with any suitable technique known in the art. For example, the subject may urinate into a urine sample container. The urine sample may be tested immediately or stored in refrigerated or non-refrigerated conditions.

In many embodiments, the urine sample is an in vitro urine sample. In some embodiments, the urine sample is an in vivo urine sample.

The urine sample may be tested in any suitable and/or convenient location. In many embodiments, the urine sample is tested in a location selected from the group consisting of point of care, a home, a toilet, a urine sample cup, a urine sample container, a catheter, a testing laboratory, a pad, a liner, and combinations thereof.

Testing may include a variety of individual steps and substeps. For example, testing may include a method selected from the group consisting of identification, detection, quantification, analysis, correlation, and combinations thereof.

Testing may include, but is not limited to, a technique selected from the group consisting of protein analysis, antibody detection, metabolomic analysis, lateral flow assays, and combinations thereof.

Testing may include, but is not limited to, a technique selected from the group consisting of liquid chromatography with tandem mass spectrometry (LC-MS-MS), gas chromatography-mass spectrometry (GC-MS), nuclear magnetic resonance (NMR), enzyme-linked immunosorbent assay (ELISA), metabolite sensing, UV-Vis detection, fluorescence, and combinations thereof.

In many embodiments, a consumer product is used to assess bladder health of a subject. In these embodiments, the consumer product comprises a sensor configured to test a urine sample from the subject tier a metabolite selected from the group consisting of androstenediol, octenedioate, dihydrouracil, heptanoylglutamine, pregnenetriol sulfate, heptenoylglutamine, hexanoylglutamine, guanine, methylhexanoylglutamine, hexanoylglycine, hexenoylgycine, spermidine, diacetylspermine, acisoga, and combinations thereof.

In some embodiments, testing comprises exposing a consumer product comprising a sensor to the urine sample. The consumer product may be selected from personal hygiene products, incontinence products, wipes, disposable bed liners, baby and adult diaper products, child training pants, feminine pads and napkins, disposable testing products, testing strips, testing pads, reusable testing products, toilet products, and combinations thereof.

In some embodiments, the consumer product produces a visible change in response to the metabolite, wherein the visible change is selected from the group consisting of a color change, a shape change, a readout, a written message, an electronic display, and combinations thereof.

EXAMPLES

Without further elaboration, it is believed that one skilled in the art using the preceding description can utilize the present invention to its fullest extent. The following Examples are, therefore, to be construed as merely illustrative, and not limiting of the disclosure in any way whatsoever.

Example 1. Metabolomic Analysis

Urine was collected from seven human subjects females aged≤65, n=7; 4 UUI/OAB, 3 asymptomatic) via transurethral catheterization. Samples were extracted and split into equal parts for analysis on LC/MS/MS and Polar LC platforms (Metabolon; Morrisville, NC, USA). Proprietary software was used to match ions to an in-house library of standards for metabolite identification and quantitation by peak area integration. Intensities of metabolites were scaled and provided for each sample in a raw data format for further statistical analysis.

Metabolite characterization returned many metabolites. Some of these metabolites were only partially characterized, identified as drugs taken by subjects, or classified as not being biologically relevant for the purpose of this disclosure. Such metabolites were filtered from the dataset allowing for a more targeted approach when using predictive modeling. This modeling allows a determination of whether OAB/UUI may be predicted by performing statistical analysis on the identified metabolites and their intensities.

To identify those metabolites which differentiate the two states, the software performs a Pearson's correlation and provides a p-value expressing the correlation between each metabolite and the response. Additionally, a variable importance value (VIP) was calculated to rank metabolites which contribute to this differentiation. Metabolites with p-values less than 0.05 and VIP values greater than 1 were considered important and used for further analysis. The remaining 326 metabolites were tested using a linear discriminant (LDA) effect size (LEfSe) method to identify 37 metabolites having intensities differing between the two states.

The 37 identified metabolites include ascorbate (Vitamin C), dehydroascorbate, CEHC-sulfate, CEHC-taurine, CEHC-glucuronide, pantoate, N,N-dimethyl-5-aminovalerate, lactonate, phenylacetylalanine, methylcatecholsulfate, phenylacetylglutamine, carboxysuccinate, carboxyethylvaline, arabinose, threonate, methylcrotonylglycine, glucuronate, carboxyethylisoleucine, glycoursodeoxycholate, leucylalanine, lithocholatesulfate, allo-threonine, cholic acid glucuronide, spermidine, androstenediol, octenedioate, dihydrouracil, heptanoylglutamine, pregenetriol sulfate, heptenoylglutamine, diacetylspermine, acisoga, hexanoylglutamine, guanine, methylhexanoylglutamine, hexanoylglycine, and hexenoylgycine. The ratio between the expression of 37 metabolites in subjects with UUI/OAB and the expression of the same 37 metabolites in healthy, asymptomatic subjects is shown below in Table 1.

TABLE 1

Relative expression of select metabolites.

| Metabolite | Expression in UUI/OAB subjects compared to healthy, asymptomatic subjects |
|---|---|
| ascorbate (Vitamin C) | 28.813 |
| dehydroascorbate | 5.858 |
| alpha-CEHC sulfate | 1.447 |
| alpha-CEHC taurine | 3.841 |
| alpha-CEHC glucuronide | 1.602 |
| pantoate | 0.969 |
| N,N-dimethyl-5-aminovalerate | 1.624 |

TABLE 1-continued

Relative expression of select metabolites.

| Metabolite | Expression in UUI/OAB subjects compared to healthy, asymptomatic subjects |
|---|---|
| galactonate | 1.043 |
| phenylacetylalanine | 1.116 |
| 4-methylcatechol sulfate | 1.174 |
| phenylacetylglutamine | 0.900 |
| carboxysuccinate | 1.091 |
| 1-carboxyethylvaline | 0.992 |
| arabinose | 1.084 |
| threonate | 0.952 |
| 3-methylcrotonylglycine | 0.909 |
| glucuronate | 1.015 |
| 1-carboxyethylisoleucine | 0.904 |
| glycoursodeoxycholate | 1.523 |
| leucylalanine | 0.606 |
| lithocholate sulfate | 1.04 |
| allo-threonine | 0.547 |
| cholic acid glucuronide | 0.947 |
| spermidine | 0.180 |
| androstenediol (3beta, 17beta) monosulfate | 0.192 |
| 4-octenedioate | 0.231 |
| 5,6-dihydrouracil | 0.200 |
| heptanoylglutamine | 0.0586 |
| pregnenetriol sulfate | 0.0613 |
| 3-heptenoylglutamine | 0.151 |
| N1,N12-diacetylspermine | 0.131 |
| acisoga | 0.136 |
| hexanoylglutamine | 0.0927 |
| guanine | 0.0933 |
| 4-methylhexanoylglutamine | 0.0551 |
| hexanoylglycine | 0.0616 |
| trans-2-hexenoylglycine | 0.0499 |

Each of the 37 identified metabolites was ranked by the effect size (influence). Upon performing filtering and statistical tests (linear discriminant analysis; LDA) on metabolites, 23 metabolites were over-represented in subjects with UUI or OAB and 14 metabolites were over-represented in asymptomatic (healthy) subjects (Table 1 and FIG. 1).

The top 14 metabolites indicative of bladder health were androstenediol, octenedioate, dihydrouracil, heptanoylglutamine, pregnenetriol sulfate, heptenoylglutamine, hexanoylglutamine, guanine, methylhexanoylglutamine, hexanoylglycine, spermidine, diacetylspermine, acisoga, and hexenoylglycine. Of these 14 metabolites, androstenediol is a very important indicator and is present in an overabundance in healthy urine. Additionally, the estrogenic activity of androstenediol provides estrogenic support, which has been shown to alleviate LUTS symptoms. Thus, the present disclosure presents a robust metabolic profile of OAB/UUI for use in urinalysis.

Example 2. Applications

Testing for metabolites identified in this disclosure may be performed according to any suitable analytical or diagnostics method known in the art. Testing of the metabolites identified in this disclosure may be performed with any suitable test, piece of equipment, technique, or technology known in the art. Testing includes identification, detection, quantification, analysis, correlation, and combinations thereof.

Testing for metabolites identified in this disclosure may be performed with methods including, but not limited to, liquid chromatography with mass spectrometry (LC-MS), liquid chromatography with tandem mass spectrometry (LC-MS-MS), gas chromatography-mass spectrometry (GC- MS), nuclear magnetic resonance (NMR), enzyme-linked immunosorbent assay (ELISA), UV-Vis detection, fluorescence, and metabolite sensing (e.g. a G protein-coupled receptor (GPCR) sensor for tricarboxylic acid (TCA) cycle metabolites).

Indicators for the metabolites identified in this disclosure may be incorporated into traditional urinalysis workflows or consumer products. Such consumer products include pads or strips for individuals to perform their own testing at home. Testing for these indicators may include protein analysis, antibody detection, metabolomic analysis, lateral flow assays, or any suitable analytical or diagnostics method known in the art.

Antibody detection may be used through the following process. Antibodies designed to bind specific metabolites are placed onto pads, liners, and/or wicking materials for lateral flow that allow the movement of antibodies. Mobile-bound antibodies interact with immobilized antibodies and allow for detection of the metabolites via color change.

Enzyme detection may be used through the following process. Specific enzymes and cofactors (e.g. NAD) that degrade or oxidize metabolites are incorporated into a material, such as a product (pads and/or liners) or a liquid. Urine is added to the material containing the enzymes and a reaction occurs. The reaction causes a color change or fluorescence, which may be detected via eye or luminometer.

GC-MS, LC-MS and/or LC-MS-MS detection may be used through the following process. A urine sample is exposed to GC or LC separation and the metabolites of interest are detected with MS. These modes of detection are particularly useful for clinical testing.

In some embodiments, sub-nanoliter mass spectrometry, or smaller scale mass spectrometry, may be used. These MS techniques operate on the same principles as conventional GC and LC-MS. These MS techniques allow miniaturization for home and/or in-product testing.

NMR detection may be used through the following process. A urine sample is provided to an NMR spectrometer and the metabolites of interest are detected with NMR. This mode of detection is particularly useful for clinical testing.

This written description uses examples to illustrate the present disclosure, including the best mode, and also to enable any person skilled in the art to practice the disclosure, including making and using any compositions or systems and performing any incorporated methods. The patentable scope of the disclosure is defined by the claims, and may include other examples that occur to those skilled in the art. Such other examples are intended to be within the scope of the claims if they have elements that do not differ from the literal language of the claims, or if they include equivalent elements with insubstantial differences from the literal language of the claims.

As used herein, the terms "comprises," "comprising," "includes," "including," "has," "having," "contains", "containing," "characterized by" or any other variation thereof, are intended to cover a non-exclusive inclusion, subject to any limitation explicitly indicated. For example, a composition, mixture, process or method that comprises a list of elements is not necessarily limited to only those elements but may include other elements not expressly listed or inherent to such composition, mixture, process or method.

The transitional phrase "consisting of" excludes any element, step, or ingredient not specified. If in the claim, such would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole.

The transitional phrase "consisting essentially of" is used to define a composition or method that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

Where an invention or a portion thereof is defined with an open-ended term such as "comprising," it should be readily understood that (unless otherwise stated) the description should be interpreted to also describe such an invention using the terms "consisting essentially of" or "consisting of."

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

As used herein, the term "about" means plus or minus 10% of the value.

What is claimed is:

1. A method of assessing lower urinary tract symptoms in a subject, the method comprising:
testing a urine sample from the subject for androstenediol and at least two metabolites selected from the group consisting of octenedioate, dihydrouracil, heptanoylglutamine, pregnenetriol sulfate, heptenoylglutamine, hexanoylglutamine, guanine, methylhexanoylglutamine, hexanoylglycine, hexenoylglycine, spermidine, diacetylspermine, acisoga, and combinations thereof;
wherein testing comprises exposing a consumer product selected from the group consisting of personal hygiene products, incontinence products, wipes, disposable bed liners, baby and adult diaper products, child training pants, feminine pads and napkins, disposable testing products, testing strips, testing pads, toilet products, and combinations thereof to the urine sample; and
producing a metabolic profile for the androstenediol and at least two metabolites; and
using the metabolic profile to assess whether the subject has a lower urinary tract symptom selected from the group consisting of overactive bladder, urinary urge incontinence, and combinations thereof.

2. The method of claim 1, wherein the method further comprises communicating the metabolic profile.

3. The method of claim 1, wherein testing comprises testing for at least four metabolites.

4. The method of claim 1, wherein the subject is a female subject.

5. The method of claim 1, wherein the urine sample is tested in a location selected from the group consisting of point of care, a home, a toilet, a urine sample cup, a urine sample container, a catheter, a testing laboratory, a pad, a liner, and combinations thereof.

6. The method of claim 1, wherein testing comprises exposing the consumer product comprising a sensor to the urine sample.

7. The method of claim 1, wherein testing comprises a method selected from the group consisting of identification, detection, quantification, analysis, correlation, and combinations thereof.

8. The method of claim 1, wherein testing comprises a technique selected from the group consisting of protein analysis, antibody detection, metabolomic analysis, lateral flow assays, and combinations thereof.

9. A consumer product for use in assessing bladder health of a subject, the consumer product comprising:
   a sensor configured to test a urine sample from the subject for androstenediol and at least two metabolites selected from the group consisting of octenedioate, dihydrouracil, heptanoylglutamine, pregnenetriol sulfate, heptenoylglutamine, hexanoylglutamine, guanine, methylhexanoylglutamine, hexanoylglycine, hexenoylglycine, spermidine, diacetylspermine, acisoga, and combinations thereof;
   wherein the consumer product is selected from the group consisting of personal hygiene products, incontinence products, wipes, disposable bed liners, baby and adult diaper products, child training pants, feminine pads and napkins, disposable testing products, testing strips, testing pads, toilet products, and combinations thereof; and
   wherein the consumer product comprises an indicator for the androstenediol and the at least two metabolites.

10. The consumer product of claim 9, wherein the consumer product produces a visible change in response to the androstenediol and at least two metabolites, wherein the visible change is selected from the group consisting of a color change, a shape change, a readout, a written message, an electronic display, a printed display, and combinations thereof.

\* \* \* \* \*